US006102035A

United States Patent [19]

Asking et al.

[11] Patent Number: 6,102,035

[45] **Date of Patent: *Aug. 15, 2000**

[54] INHALER

[75] Inventors: Lars Asking; Kjell Bäckström, both of Lund; Henri Hansson, Dösjebro; Magnus Jahnsson, Lund; Richard Lindahl, Malmö , all of Sweden

[73] Assignee: Astra Aktiebolag, Sodertaje, Sweden

[ * ] Notice: This patent issued on a continued prosecution application filed under 37 CFR 1.53(d), and is subject to the twenty year patent term provisions of 35 U.S.C. 154(a)(2).

[21] Appl. No.: 08/817,233

[22] PCT Filed: Jul. 23, 1996

[86] PCT No.: PCT/SE96/00970

§ 371 Date: Apr. 10, 1997

§ 102(e) Date: Apr. 10, 1997

[87] PCT Pub. No.: WO97/05918

PCT Pub. Date: Feb. 20, 1997

[30] Foreign Application Priority Data

Aug. 10, 1995 [SE] Sweden .................................. 9502800

[51] Int. Cl.[7] .................................................... A61M 15/00

[52] U.S. Cl. ................................ 128/203.15; 128/203.12

[58] Field of Search ......................... 128/203.15, 203.21, 128/203.12

[56] References Cited

U.S. PATENT DOCUMENTS

| | | | |
|---|---|---|---|
| 598,286 | 2/1898 | Curran | 128/203.15 |
| 1,696,469 | 12/1928 | Campbell | 128/203.15 |
| 2,470,296 | 5/1949 | Fields | 128/203.15 |
| 2,573,918 | 11/1951 | McCuiston | 128/203.15 |
| 2,642,063 | 6/1953 | Brown | 128/203.15 |
| 4,046,146 | 9/1977 | Rosskamp et al. | 128/203.15 |
| 4,105,027 | 8/1978 | Lundquist | 128/203.15 |
| 4,192,309 | 3/1980 | Poulen | 128/203.15 |
| 4,534,345 | 8/1985 | Wetterlin | 128/203.15 |
| 4,907,583 | 3/1990 | Wetterlin et al. | 128/203.15 |
| 5,042,472 | 8/1991 | Bunin | 128/203.15 |
| 5,239,991 | 8/1993 | Chawla et al. | 128/203.15 |
| 5,331,953 | 7/1994 | Andersson et al. | 128/203.15 |
| 5,349,947 | 9/1994 | Newhouse et al. | 128/203.21 |
| 5,447,151 | 9/1995 | Bruna et al. | 128/203.15 |
| 5,460,173 | 10/1995 | Mulhauser et al. | 128/203.15 |
| 5,533,505 | 7/1996 | Källstrand et al. | 128/203.15 |
| 5,655,523 | 8/1997 | Hodson et al. | 128/203.15 |
| 5,660,169 | 8/1997 | Källstrand et al. | 128/203.15 |

FOREIGN PATENT DOCUMENTS

| | | | |
|---|---|---|---|
| 0558879 | 9/1993 | European Pat. Off. | 128/203.21 |
| WO 92/04069 | 3/1992 | WIPO . | |
| WO 93/17728 | 9/1993 | WIPO . | |

OTHER PUBLICATIONS

PCT International Search Report; Jul. 23, 1996.

PCT International Preliminary Examination Report; Jul. 23, 1996.

*Primary Examiner*—Aaron J. Lewis

*Attorney, Agent, or Firm*—Fish & Richardson P.C.

[57] ABSTRACT

A single-use, disposable inhaler comprising: (1) a housing open at both ends, one end forming an air inlet and the other forming an air outlet, thereby defining an air flow path through the inhaler; and (2) an internal plate spaced above and below the housing, oriented parallel to the axis of the inhaler and parallel to the air flow path. The internal plate comprises a storage cavity formed therein, located near the air inlet, in which a single dose of a pharmaceutically active compound is placed. An individual using the inhaler inhales through the air inlet, creating an air stream which lifts the powder out of the storage cavity, into the air stream, and to the user.

23 Claims, 4 Drawing Sheets

95
94
93
73
2
72
102
71
91,92
83
82
3
65
64
63
62
8
103
81
109
61

INHALER

THE INVENTION

The present invention relates to a disposable inhaler comprising a tubular housing forming an air flow path being open at both ends, one end forming an air inlet and one end forming an air outlet, said housing comprising a compartment for storing a pharmaceutically active substance to be inhaled, said compartment being placed in the air flow path close to the air inlet.

Inhalers of the above mentioned type are intended to carry a unit dose (i.e., single dose) of a powdered pharmaceutically active substance or a mixture including such substance whereby the particle size of the dose to be inhaled is smaller than 10 $\mu$m, preferably smaller than 5 $\mu$m.

BACKGROUND OF THE INVENTION

Disposable, breath-actuated inhalers are known in the prior art. In most of the known inhalers the powder to be inhaled is loosely provided in the inhalation channel as can be seen in for example in EP-A-0 404 454 and U.S. Pat. No. 4,265,236.

In the known above-mentioned devices the powder is provided loosely in a relative large chamber which functions as powder compartment and inhalation channel being provided with air inlet and outlet. The powder in the inhalation devices of the above-mentioned type has a particle size which is generally smaller than 10 $\mu$m whereby strong cohesive forces are present between the powder particles. These cohesive forces causes the creation of aggregates of powder which are created during handling and storage of the inhaler. When the powder is freely movable within a chamber as in the above mentioned documents an uncontrolled creation of aggregates will occur. These aggregates could either be to big to be inhaled or too big to enter into the bronchial region of the patient, e.g. larger than 10 $\mu$m. With the powder freely movable within a chamber the powder will also stick to the walls due to the adhesive forces between the particles and the walls as well as to electrostatic forces occurring in the device.

These drawbacks are solved in the inhalation devices as described in WO 92/04069 and WO 93/17728. In the constructions according to these applications the powder is provided in a compartment which is provided as an indent or cavity in the lower part of the housing of the inhaler. The powder compartment, the cavity, is provided close to the air inlet, and the air flow path is provided with a constriction adjacent the powder compartment in order to create an acceleration of the air flow to lift the powder dose out of the cavity and mix it with the inhalation air flow during inhalation. In WO 93/17728 a hole is provided in the cavity in order to facilitate the lifting of the dose into the inhalation air flow. In order to break down the aggregates of the powder dose into respirable particles the inhalers as described in these two applications are provided with deaggregation means provided within the air flow path.

The cavity and thereby the powder dose is protected before inhalation by two tapes, one covering the upper opening of the cavity and the other covering the hole in the lower part of the cavity thereby providing a moisture proof device.

However, the construction of the known devices is provided with several disadvantages.

The inhalers according to the above mentioned applications are constructed with a housing having an upper and a lower part sealed to each other wherein the two parts are made of different materials. The upper part is made of plastic material whereas the lower part in which the powder compartment or cavity is placed is made of aluminium or a laminate of aluminium and plastics. Furthermore, the cavity and thereby the hole in the cavity are provided in an unprotected manner and the cavity can easily be damaged during handling and storage of the inhalers. Moreover, as the hole is provided in the lower part of the cavity it is easily covered by a user's thumb or hand during inhalation whereby the function of the inhaler is jeopardised as the dose or parts of the dose may not be properly lifted out of the cavity.

These disadvantages are solved by the inhalation device according to the present invention.

The present invention provides a disposable breath-actuated dry-powder inhalation device of the above mentioned kind wherein the disadvantages of the known devices are eliminated.

The present invention also provides a construction which is more stable and rigid than the prior devices. It is also cheap and easy to produce and uses as little aluminium or laminates of aluminium as possible in order to minimise the stress to the environment The inhalation device according to the invention could be manufactured in a transparent material in order to make it possible for the patient to inspect the inhalation device and the dose before and after inhalation.

The above objects of the present invention are achieved by the features set out in claim 1, whereby the powder compartment is formed as a cavity or indent in a plate and placed in the housing in the air flow path.

In the present inhalation device the hole in the powder compartment/cavity is protected and can not be damaged during handling and storage and/or be covered during inhalation.

Further advantages and objects are clear from the features as set forth in the appended claims.

BRIEF DESCRIPTION OF THE DRAWINGS

The device according to the present invention will now be described by way of example with reference to the appended drawings, wherein.

DETAILED DESCRIPTION OF THE DRAWINGS

Figure 1:
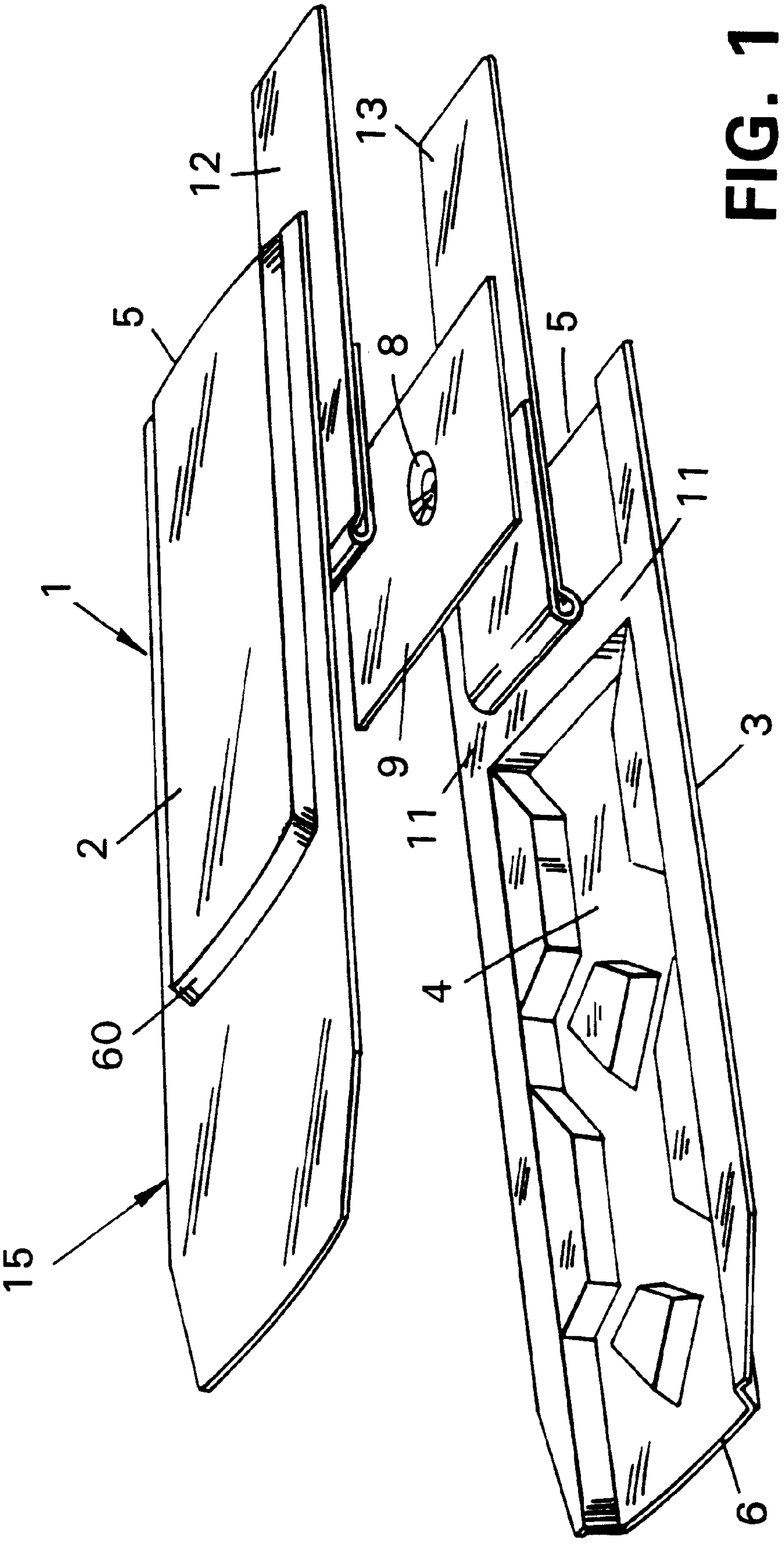
FIG. 1 shows an exploded view of a first embodiment of the present invention.

A preferred embodiment of the invention will now be described with reference to FIGS. 1, 2 and 3.

Figure 2:
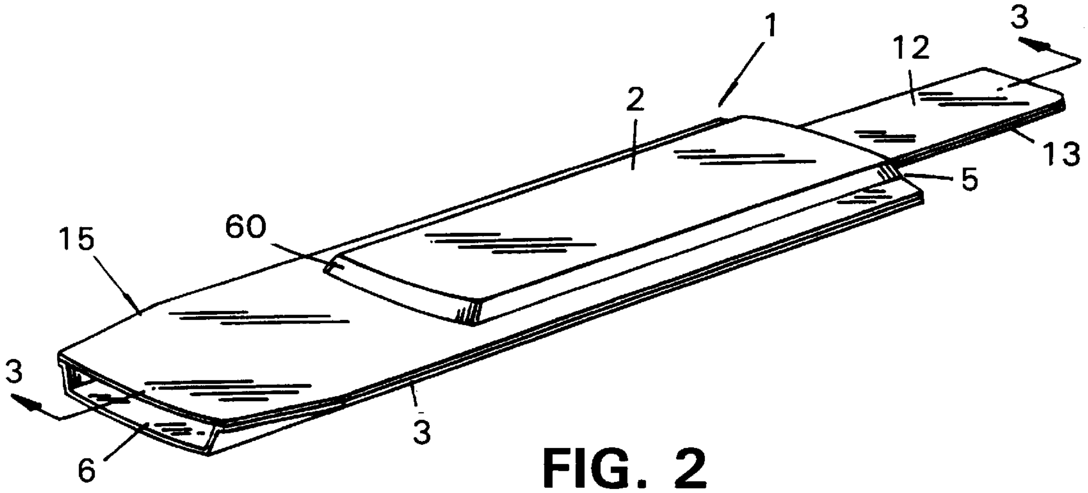
FIG. 2 shows a schematic side view of the first embodiment as shown in FIG. 1.
Figure 3:
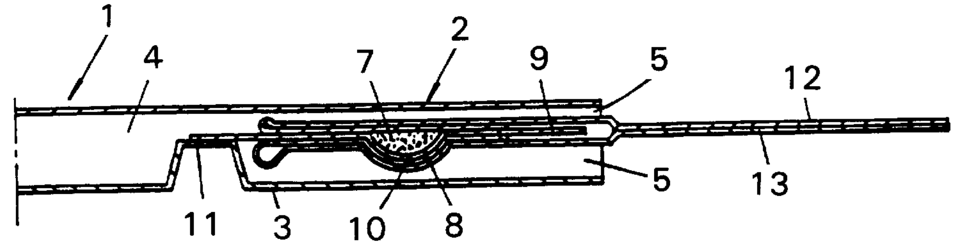
FIG. 3 shows a cross-sectional view taken at 3—3 of FIG. 2 of the first embodiment as shown in FIG. 1.

As can be seen in FIG. 2 the inhalation device according to the invention comprises a substantially tubular housing 1 being substantially symmetrical around its longitudinal centre axis. Said housing consist of two parts, an upper part 2 and a lower part 3 being sealed together at their respective edges thereby forming an air flow path 4 for the inhalation air flow. Said air flow path 4 is opened at both ends whereby one end forms an air inlet 5 and the second end forms an air outlet 6.

The sealing of the upper part 2 and lower part 3 may be effected in any known manner such as ultra sonic welding or heat sealing but also by gluing or by use of any other suitable sealing method. Said upper part 2 and lower part 3 are preferably formed of the same material such as polyethylene, polypropylene, polyester, polystyrene or similar and are preferably formed by heat-forming but any other methods may be used such as moulding. It is preferred that at least the upper part or top of the inhalation device is transparent in order to make it possible for the user to inspect the inhaler and the air flow path after inhalation to see whether the dose has been properly released and inhaled. The dose can also be inspected before inhalation.

A dose 7 to be inhaled is placed in a cavity 8. Said cavity is provided in a substantially flat plate 9. Said plate 9 is formed as an insert which is placed during manufacture of the device between the upper part 2 and lower part 3 of the housing 1 in the air flow path 4 close to the air inlet 5 of the inhaler. The cavity is substantially formed as a sphere segment and is preferably provided with one hole in or a group of holes 10 arranged around the centre of the segment.

Said lower part 3 is provided with a support surface 11 for the plate 9. Said support surface 11 is provided as a frame having three sides on which the plate 9 is placed as can be seen in FIGS. 1 and 3. The open end of the support surface 11 is directed towards the air inlet 5 of the device. The air inlet allows air to enter both above and under the plate 9 and the cavity 8 as can be seen in FIG. 3. The air entering over the cavity creates a pressure difference between the region above and the region below the cavity 8 thereby facilitating the release, e.g. lifting, of the dose out of the cavity. If the cavity is provided with a hole 10 or a group of holes, a small amount of air will enter into the hole/holes thereby further improving the release of the dose.

The plate 9 is preferably made of aluminum or a laminate of aluminum and plastic sheet, and the cavity is formed conveniently in the plate by a using cold-forming procedure before the plate is placed in the housing.

After the cavity 8 has been formed in the plate 9 the powdered substance to be inhaled is filled into the cavity. When filling the substance an exact amount of substance must be metered and filled into the cavity and compacted to the desired degree in order to provide an exact dose so that the inhaler can function correctly. This can be achieved by using the method described in the International patent application PCT/SE95/00109.

In order to seal the dose 7 in the cavity 8 the cavity is covered by a first removable 12 sealing tape. If the cavity 8 is provided with a hole 10 a second removable sealing tape 13 is provided to cover said hole or each hole if more than one is present. It is of utmost importance to provide a moisture proof sealing for the dose in the cavity as most finely divided powdered substances are not stable if subjected to moisture. The removable sealing tapes provide a sealing and a cover for the dose during handling and storage and the tape or the tapes can be easily removed before inhalation. The first and second tapes are placed in position directly after the filling of powdered substance into the cavity. The tape is preferably made of laninates of plastic materials and aluminum but any other suitable material can be used.

The upper surface of the upper part 2 in the preferred embodiment forms a mouth piece 15 with the end portion of the lower part 3 around air outlet 6. The said upper surface of the upper part 2 may be provided with a guidance of how far the inhaler shall be inserted into the mouth of the user. A guiding element 60 is formed by shaping the upper part 2 and this guiding element reduces the cross-section of the air flow path at a distance from the air outlet and the position of the dose. Tests have shown that such reduction of the cross-section of the air flow path can be positioned at a distance of about 2 to 4 cm along the length seen from the air outlet 5 without giving rise to any negative effect on the flow characteristics of the device.

In order to break down substance in the form of aggregates into primary particles during inhalation deaggregation means are provided in the air flow path.

In the first preferred embodiment several sets of oblique planar surfaces are provided along the path of the air flow. Said surfaces provide constrictions in the air flow path which will increase the speed of inhalation air flow during its passage out along the air flow path. The surfaces or walls of the deaggregation means are disposed generally perpendicular to a plane through the longitudinal axis of the tubular housing and cover the whole cross-section of the housing. Aggregates and/or particles will thereby be forced to impact on the walls of the housing and the surfaces provided in the air flow path.

Tests have shown that the breakdown of aggregates into the primary particles is related to the positions and angles of said surfaces as well as the dimensions of the cross sections of the air flow path at different positions. A preferred embodiment of the deaggregation means will be described with reference to FIGS. 4, 4a and 4b.

In the preferred embodiments the deaggregation means have substantially two different forms and constructions.

The first deaggregation means 20a, 20b and 30a, 30b are formed as bodies having pairs of surfaces or walls 21a, 21b and 31a, 31b respectively, extending with an angle $\alpha_a$ and $\alpha_b$, respectively, to the main direction of the air flow and the longitudinal centre axis of symmetry of the air flow path and the device seen from the air inlet to the air outlet. Said longitudinal centre axis is marked with X—X in FIGS. 4, 4a and 4b. Said pairs of walls extend from the edges of the housing on both sides of the air flow path symmetrically and are spaced apart so as to provide a passage for the air flow and a restriction in the air flow path. The first pair of walls 21a, 21b are placed adjacent the release area of the dose 7. Said pairs of walls 21a, 21b and 31a, 31b are connected to a part 22a, 22b and 32a, 32b respectively being longitudinal in the direction of the air flow. Said longitudinal parts extend parallel to the main direction of the air flow and are spaced apart so as to provide a passage for the air flow. The other end of said longitudinal parts 22a, 22b and 32a, 32b are connected to walls 23a, 23b and 33a, 33b respectively which together with the first wall and the longitudinal part of each deaggregation means substantially form a quadrangle 20a, 20b, 30a, 30b respectively, see FIG. 4. In FIG. 4a this preferred embodiment is shown schematically.

Figure 4:
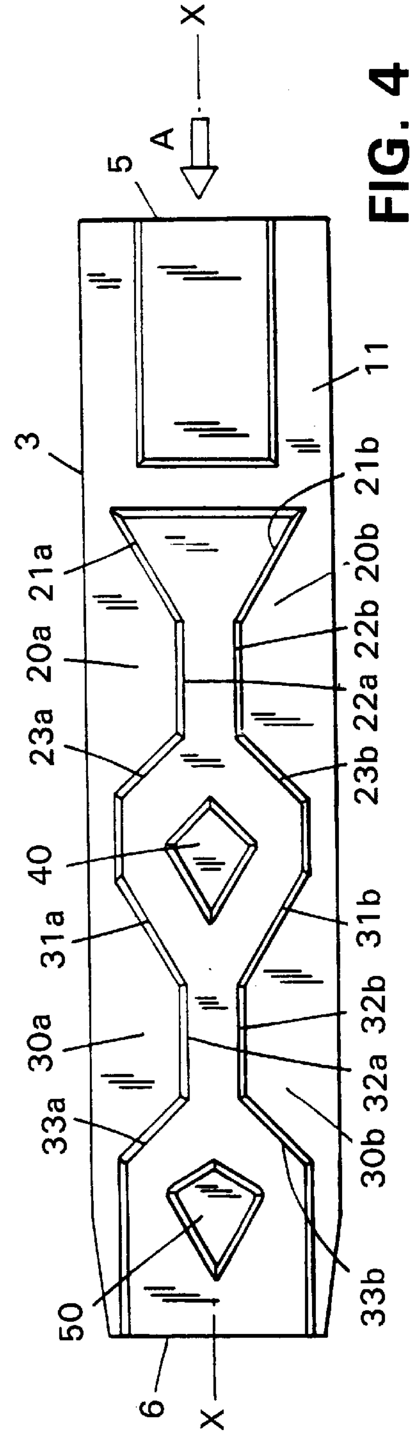
FIG. 4 shows a preferred embodiment of the deaggregation means placed in the air flow path of an inhaler according to the present invention.
Figure 4B:
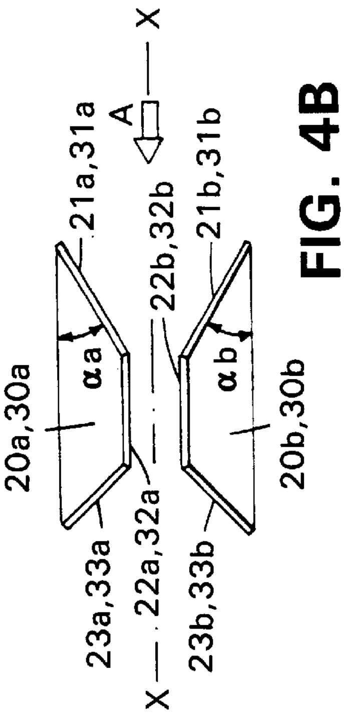
FIG. 4*b* shows the second deaggregation means as shown in FIG. 4.
Figure 4A:
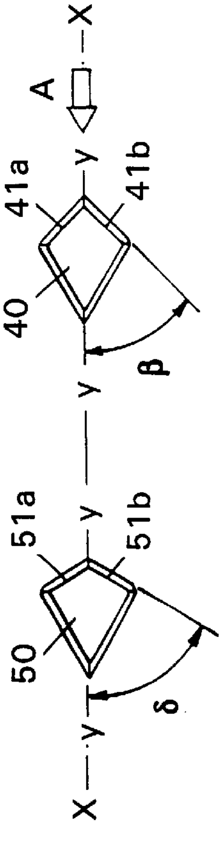
FIG. 4*a* shows the first deaggregation means.
Figure 5:
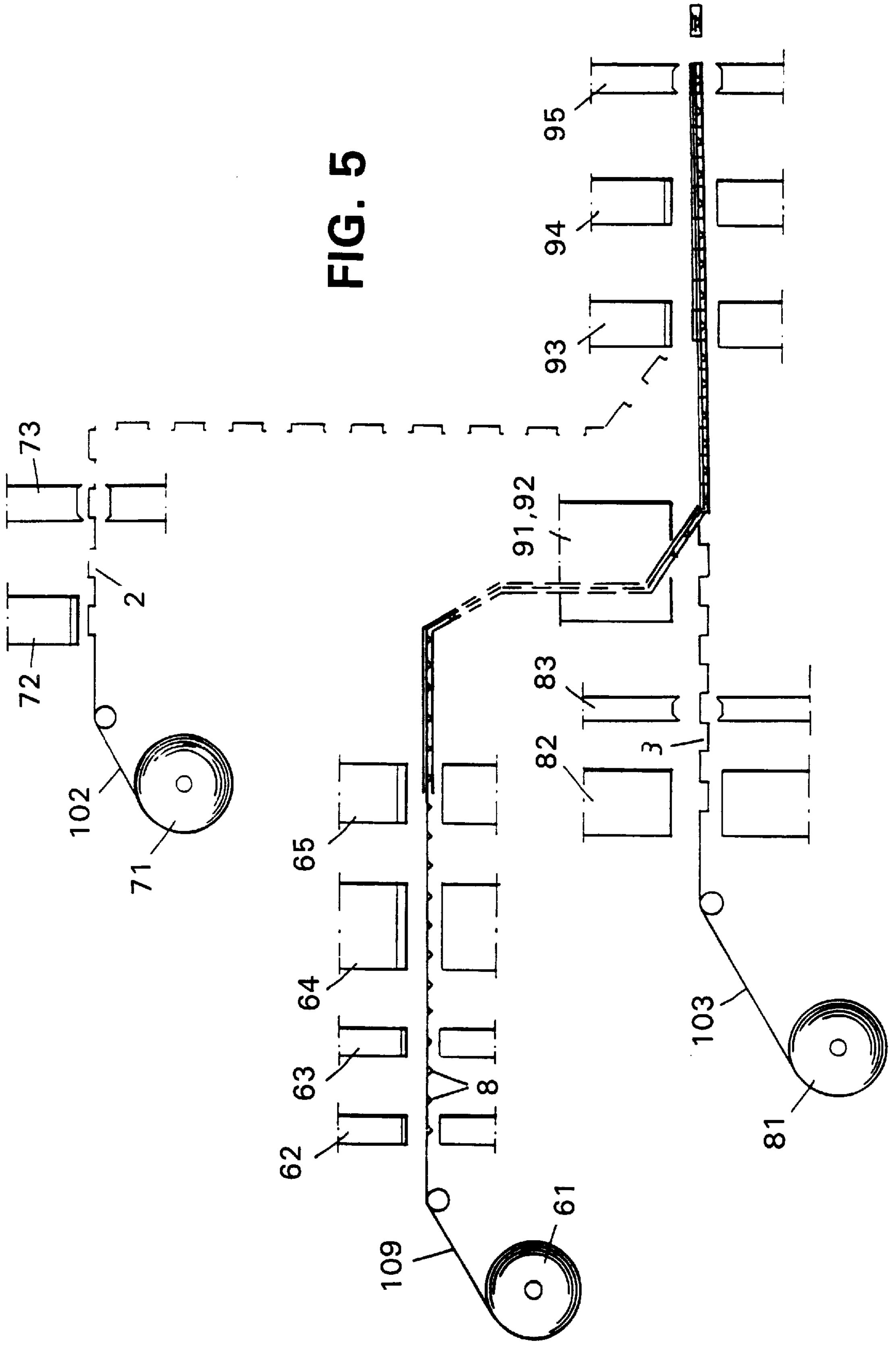
FIG. 5 shows schematically a method of producing the inhalation device as described in FIGS. 1 to 4.

The second deaggregation means 40, 50 are also formed as bodies having pairs of surfaces or walls preferably provided as quadrangles being symmetrical around their longitudinal axis as can be seen in FIGS. 4 and 4b. They are provided in the centre of the air flow path 4 and the longitudinal axis of symmetry y—y of the quadrangles 40, 50, coinciding with the longitudinal axis of symmetry X—X of the housing 1 and thereby the air flow path 4. Said quadrangles 40 and 50 are formed with a pair of surfaces or walls 41*a,* 41*b* and 51*a,* 51*b* respectively. The walls 41*a,* 41*b* and 51*a,* 51*b* in each quadrangle 40 and 50 are connected to each other at an angle which is directed to the centre axis of the main direction of the air flow seen from the air inlet to the air outlet and placed on the axis of symmetry of the housing. Two walls 41*a,* 41*b* and 51*a,* 51*b* are thereby placed with angles $\beta$ and $\delta$, respectively, to the main direction of the air flow and the longitudinal axis of symmetry of the air flow path and the device seen from the air inlet to the air outlet. The preferred embodiment of the second deaggregation means 40 and 50 are shown in FIGS. 4 and 4*b*.

The first and second deaggregation means 20*a,* 20*b,* 30*a,* 30*b* and 40, 50 are positioned in the air flow path in a manner which gives rise to acceleration areas for the air flow and the aggregates/particles as well as guidance whereby the aggregates and/or particles are forced to impact on the walls of said deaggregation means.

The form of the deaggregation means has been determined by tests and the most optimal forms for the above mentioned purpose have shown to be the ones represented in FIG. 4. The forms of the deaggregation means are also of importance for non-retention of substance in the air flow path as well as for the air flow resistance of the inhaler.

The tests have shown that the values of the angles $\alpha_a$, $\alpha_b$ and $\beta$, $\delta$ are of utmost importance for the function of the deaggregation means and thereby the function of the inhaler. Several tests have been carried out with different substances and the values of the angles have been determined out of an optimisation of the different parameters which influence the performance of the air flow during inhalation. It has thereby been important to minnimise the retention and the flow resistance as well as maximise the deaggregation at a typical air flow rate which depends on the inhalation force of a patient using the inhalation device.

The tests have shown that the $\alpha_a$ and $\alpha_b$ should be substantially about 30° to the main direction of the air flow seen from the air inlet to the air outlet and to a longitudinal axis being parallel to the longitudinal axis of symmetry of the device.

The value of the angle $\beta$ is substantially about 45° to the main direction of the air flow seen from the air inlet to the air outlet and to the longitudinal axis of the device.

The value of the angle $\delta$ is substantially about 60° to the main direction of the air flow seen from the air inlet to the air outlet and to the longitudinal axis of the device.

When the inhaler is to be used, the inhaler is held more or less horizontal with the lower part 3, i.e. the part on which the plate 9 with the cavity 8 containing the dose 7 is placed, facing downwards. The free end of the sealing tape 12, and if a hole 10 is provided in the cavity 8, sealing tape 13 is pulled outwardly and the powder in the powder compartment 8 is exposed. The user then inserts the air outlet 6 which in one preferred embodiment is formed as a mouth piece 15 into the mouth until the upper lip is in contact with the guiding element 60 and inhales through the inhaler. The resultant air flow through the inhaler will become very turbulent in the region of the cavity and the dose of pharmaceutical powder will be lifted out of the powder compartment and mixed with the air-flow. Any aggregates created in the powder dose will impact on the planar surfaces of the deaggregation means and break down into primary particles.

The inhaler according to the invention is preferably manufactured and filled by using a method as described in the above mentioned International patent application PCT/SE95/00109. Said method can easily be modified to be used to manufacture a disposable inhaler according to the present invention.

The plate 9 is formed from an elongate layer of a first material 109 provided from a first roller 61. The cavities 8 are formed as spherical segments at predetermined spaces from each other along the length of the elongate layer in a forming station 62. In the embodiment in which a hole 10 or a group of holes is provided in the cavity this hole or these holes are punched out in or around the centre of the sphere segment forming the cavity either when the cavity is formed or in a punching station 63. In the following filling station 64 a pharmaceutically active substance is filled into the cavities one by one and compacted by using the method described in the above mentioned International patent application. After the filling of a cavity, the cavity and the dose are covered by at least a first sealing tape 12. Said first sealing tape 12 is provided as a cover on the upper side of the cavity. In the embodiment with a hole or a group of holes provided in the cavity a second sealing tape 13 is provided at the bottom or back side of the cavity thereby covering the hole or group of holes in the cavity. Both of these tapes are provided in the same step in the tape station 65.

The housing 1 of the inhaler is formed in separate production lines by providing a second elongate layer 102 and a third elongate layer 103 of material from a second roller 71 and a third roller 81. Said second elongate layer 102 and third elongate layer 103 are formed to the upper part 2 and lower part 3 of the housing respectively in forming stations 72 and 82. Thereby preferably the upper part 2 is formed with the mouth piece 15 and the guiding element 16 as described above. The lower part 3 is formed with the support surface 11 for the plate 9 and the deaggregation means 20*a,* 20*b;* 30*a,* 30*b;* 40; 50 as described above.

After the forming of the upper part 2 and lower part 3, they are cut into predetermined pieces in cutting stations 73 and 83 respectively.

The lower part 3, in which the support surface 11 and the deaggregation means 20*a,* 20*b;* 30*a,* 30*b;* 40; 50 have been formed, is moved to a station 91 where the elongate layer 109, in which plates 9 with cavities 8 have been formed, filled and sealed in a parallel production line, are continously placed on the support surfaces 11 of the lower part 3. The plates 9 are fixed to the corresponding lower part 3 of the housing by using any known suitable method such as gluing, isostatic pressing, heat sealing or welding, e.g. laser-, ultra sonic-, heat- or cold-welding in a fixing station 92. The lower parts 3 moved to a station 93 where the upper parts 2 is placed on top of said lower parts 3 with the plates 9, whereby an upper part 2 of the inhaler is placed on a corresponding pre-formed lower part 3 in such a manner that the housing of the inhalation device is formed.

Said upper part 2 and lower part 3 are thereafter sealed together in a sealing station 94. Also here any known sealing/fixing method can be used such as gluing, heat sealing or welding methods such as e.g. laser-, ultra sonic-, heat- or cold-welding. Thereafter the devices, still being in the form of a continuos layer, are moved to a further cutting station 95 where the excess material from the plates are cut away and the inhalation devices are separated from each other. The disposable inhalers according to the present invention are thereby formed.

The inhalation device of the present invention is intended to be used with any substances suitable for administration, i.e. any substances which may be administered by inhalation. Suitable inhalable medicaments may include for example β2-adrenoreceptor agonists for example salbutamol, terbutaline, rimiterol, fenoterol, reproterol, adrenaline, pirbuterol, isoprenaline, orciprenaline, bitolterol, salmeterol, formoterol, clenbuterol, procaterol, broxaterol, picumeterol, TA-2005, mabuterol and the like, and their pharmacologically acceptable esters and salts; anticholinergic bronchodilators for example ipratropium bromide and the like; glucocorticosteroids for example beclomethasone, fluticasone, budesonide, tipredane, dexamethasone, betamethasone, fluocinolone, triamcinolone acetonide, mometasone, and the like, and their pharmacologically acceptable esters and salts; anti-allergic medicaments for example sodium cromoglycate and nedocromil sodium; expectorants; mucolytics; antihistamines; cyclooxygenase inhibitors; leukotriene synthesis inhibitors; leukotriene antagonists, phospholipase-A2 (PLA2) inhibitors, platelet aggregating factor (PAF) antagonists and prophylactics of asthma; antiarrhythmic medicaments, tranquilisers, cardiac glycosides, hormones, anti-hypertensive medicaments, antidiabetic- antiparasitic- and anticancer- medicaments, sedatives and analgesic medicaments, antibiotics, antirheumatic medicaments, immunotherapies, antifungal and antihypotension medicaments, vaccines, antiviral medicaments, proteins, polypeptides and peptides for example peptide hormones and growth factors, polypeptides vaccines, enzymes, endorphines, lipoproteins and polypeptides involved in the blood coagulation cascade, vitamins and others, for example cell surface receptor blockers, antioxidants, free radical scavengers and organic salts of N,N'-diacetylcystine.

Modifications

The disposable inhaler according to the invention as described above can of course be modified within the scope of the appended claims.

Thus the upper part 2 of the housing can be formed without a guidance for the user of how far the inhaler shall be inserted into the mouth.

Furthermore, in the preferred embodiment the first and second deagglomeration means are formed as quadrangles having the described form. It is however clear that the form of the deagglomeration means can be varied. The important characteristics of the deagglomeration means are the angles of the walls in relation to the main direction of the air flow. The "backside" of the deagglomeration means could have any form which do not give rise to an increased retention of substance and a restriction of the speed of the air flow.

The values of angles $\alpha_a$, $\alpha_b$ and β, δ may be changed although the performed tests show that the most optimum values of these angles are the ones as claimed in the appended claims and stated above.

In the preferred embodiment the mouth piece is formed in the upper part of the housing and the support surface for the plate and the deaggregation means are formed in the lower part of the housing. This could of course be changed and the mouth piece, the guiding element, the support surface and the deaggregation means could be formed in any of the parts of the housing. The deaggregation means could also be formed as inserts being pre-formed and inserted into the air flow path of the housing.

What is claimed is:

1. A single-use disposable inhaler comprising:

a housing comprising an air inlet and an air outlet arranged to define an air flow path through the housing; and a compartment within the housing for storing a pharmaceutically active powder to be inhaled, said compartment being disposed in the air flow path close to the air inlet and comprising a plate supported by said housing and having a storage cavity formed therein, said plate being oriented parallel to a longitudinal axis of the inhaler and spaced from said housing both above and below said plate.

2. The disposable inhaler of claim 1, wherein said cavity includes at least one hole constructed to allow air to enter the cavity and lift the powder out of the compartment so that the powder mixes with an air stream through said air flow path during inhalation.

3. The disposable inhaler of claim 1 wherein said housing comprises an upper part and a lower part that are sealed together along their longitudinal edges.

4. The disposable inhaler of claim 3 wherein the upper and lower parts of the housing, in the vicinity of the air outlet, define a mouthpiece constructed to be placed in the mouth of a patient when the powder is to be inhaled.

5. The disposable inhaler of claim 4 further comprising a guide disposed in said upper part at said mouthpiece and constructed to assist the patient in positioning the mouthpiece in the mouth for inhalation.

6. The disposable inhaler of claim 3 wherein the upper and lower parts are generally flat.

7. The disposable inhaler of claim 1 wherein a deaggregator is provided in the air flow path between the compartment and the air outlet.

8. The disposable inhaler of claim 7 wherein said deaggregator is constructed to provide constrictions and extensions in said air flow path, providing guidance and acceleration to the air flow and the powder mixed in the air flow during inhalation.

9. The disposable inhaler of claim 1 further comprising a first removable sealing tape disposed on the plate covering the cavity and the powder therein.

10. The disposable inhaler of claim 1 wherein said inhaler is a dry powder inhaler.

11. The disposable inhaler of claim 10 wherein said dry powder inhaler is a breath-actuated inhaler.

12. The disposable inhaler of claim 1 wherein the housing is generally flat.

13. The disposable inhaler of claim 1 wherein the plate traverses the housing in a direction perpendicular to the longitudinal axis, defining an air flow region above the plate and an air flow region below the plate.

14. The disposable inhaler of claim 13 wherein inhalation through the air inlet creates an air flow both above and below the plate, creating a pressure difference between the region above the plate and the region below the plate.

15. The disposable inhaler of claim 14 wherein the cavity contains the pharmaceutically active powder, and the pressure difference facilitates release of the powder from the cavity to the air flow.

16. A single-use disposable inhaler comprising:

a housing comprising an air inlet and an air outlet arranged to define an air flow path through the housing;

a compartment within the housing for storing a pharmaceutically active powder to be inhaled, said compartment being disposed in the air flow path close to the air inlet and comprising a plate supported by said housing and having a storage cavity formed therein, said plate being oriented parallel to the axis of the inhaler and spaced from said housing both above and below said plate; and a deaggregator provided in the air flow path between the compartment and the air outlet, said deaggregator being constructed to provide constrictions and extensions in said air flow path, providing guidance and acceleration to the air flow and the powder mixed in the air flow during inhalation, wherein said deaggregator comprises a plurality of substantially planar surfaces or walls that are disposed substantially perpendicular to a plane taken through the longitudinal axis of the housing, a projection of said surfaces onto an axial cross-section of the housing substantially covering said cross-section.

17. The disposable inhaler of claim 16 wherein said deaggregator comprises a plurality of pairs of planar surfaces extending from the edges of the housing on both sides of the air flow path, each pair of said planar surfaces being oriented at angles $\alpha_a$, $\alpha_b$ relative to the longitudinal direction of the housing from the air inlet to the air outlet.

18. The disposable inhaler according to claim 17 wherein each of the angles $\alpha_a$, $\alpha_b$ is about 30°.

19. The disposable inhaler of claim 17 wherein said deaggregator further comprises a plurality of second pairs of planar surfaces positioned symmetrically around the longitudinal center axis of the housing and oriented at angles $\beta$ and $\delta$ respectively, relative to the longitudinal direction of the housing from the air inlet to the air outlet.

20. The disposable inhaler of claim 19 wherein the angle $\beta$ is about 45° and the angle $\beta$ is about 60°.

21. A single-use disposable inhaler comprising:

a housing comprising an air inlet and an air outlet arranged to define an air flow path through the housing;

a compartment within the housing for storing a pharmaceutically active powder to be inhaled, said compartment being disposed in the air flow path close to the air inlet and comprising a plate supported by said housing and having a storage cavity formed therein, said plate being oriented parallel to the axis of the inhaler and spaced from said housing both above and below said plate; and a first removable sealing tape disposed on the plate covering the cavity and the powder therein, wherein said cavity includes at least one hole constructed to allow air to enter the cavity and lift said powder out of said compartment, and said device further comprises a second removable sealing tape disposed on the opposite side of the plate covering the at least one hole provided in the cavity.

22. A method of treating a patient comprising:

(a) providing a single-use disposable inhaler comprising (i) a housing comprising an air inlet and an air outlet arranged to define an air flow path through the housing, and (ii) a compartment within the housing for storing a pharmaceutically active powder to be inhaled, said compartment being disposed in the air flow path close to the air inlet and comprising a plate supported by said housing having a storage cavity formed therein, said plate being oriented parallel to a longitudinal axis of the inhaler and spaced from said housing both above and below said plate; and (b) causing a patient to inhale through said inhaler.

23. The method of claim 22 further comprising selecting said pharmaceutically active powder to comprise a peptide or a polypeptide.

* * * * *